United States Patent
Ouyang et al.

(10) Patent No.: US 11,186,819 B2
(45) Date of Patent: Nov. 30, 2021

(54) METHODS OF SERUM-FREE CULTURING CORNEAL LIMBAL STROMAL STEM CELLS AND INDUCING SPHERE FORMATION AND DIFFERENTIATION IN VITRO

(71) Applicant: ZHONGSHAN OPHTHALMIC CENTER, SUN YAT-SEN UNIVERSITY, Guangdong (CN)

(72) Inventors: Hong Ouyang, Guangdong (CN); Liqiong Zhu, Guangdong (CN)

(73) Assignee: ZHONGSHAN OPHTHALMIC CENTER, SUN YAT-SEN UNIVERSITY, Guangdong (CN)

(*) Notice: Subject to any disclaimer, the term of this patent is extended or adjusted under 35 U.S.C. 154(b) by 468 days.

(21) Appl. No.: 16/161,246

(22) Filed: Oct. 16, 2018

(65) Prior Publication Data
US 2019/0376025 A1 Dec. 12, 2019

(51) Int. Cl.
*C12N 5/00* (2006.01)
*C12N 5/079* (2010.01)

(52) U.S. Cl.
CPC .......... *C12N 5/0018* (2013.01); *C12N 5/0621* (2013.01); *C12N 2500/42* (2013.01); *C12N 2501/11* (2013.01); *C12N 2501/998* (2013.01); *C12N 2501/999* (2013.01)

(58) Field of Classification Search
None
See application file for complete search history.

(56) References Cited

U.S. PATENT DOCUMENTS

2015/0376573 A1* 12/2015 Lee ................... A61P 43/00
424/93.7

FOREIGN PATENT DOCUMENTS

WO  WO2015108944  *  2/2015
WO  WO2017023955  *  2/2017

OTHER PUBLICATIONS

Wu et al ( Biomaterials, 2012, v.33, pp. 1343-1352.*

* cited by examiner

*Primary Examiner* — Michail A Belyavskyi
(74) *Attorney, Agent, or Firm* — Casimir Jones, S.C.; Tanya A. Arenson

(57) ABSTRACT

Provided is a method of serum-free culturing corneal limbal stromal stem cells and inducing them to differentiate and form spheres. Also provide is a medium combination for inducing corneal limbal stromal stem cells to form spheres or differentiate into corneal limbal stromal cells in vitro. The serum-free medium combination used herein can provide sufficient nutrients and a good environment required for cell growth and proliferation, can provide a stable in vitro expansion of corneal limbal stromal stem cells and can ensure that the expanded corneal limbal stromal stem cells keep their stemness and specificity. In addition, a system for inducing them to differentiate into corneal limbal stromal cells is successfully built. It can be used in experimental studies of corneal limbal stromal stem cells, cell therapy of corneal lesions and transplant for corneal injury.

14 Claims, 4 Drawing Sheets

FN

METHODS OF SERUM-FREE CULTURING CORNEAL LIMBAL STROMAL STEM CELLS AND INDUCING SPHERE FORMATION AND DIFFERENTIATION IN VITRO

CROSS REFERENCE TO RELATED APPLICATIONS

This application claims priority to Chinese Patent Application No. CN2018105746670, filed on Jun. 6, 2018 with the State Intellectual Property Office of the People' Republic of China and entitled "Methods of Serum-Free Culturing Corneal Limbal Stromal Stem Cells and Inducing Sphere Formation and Differentiation in Vitro", the contents of which are herein incorporated by reference in their entirety.

TECHNICAL FIELD

The present disclosure relates to the technical field of cell engineering. More specifically, the present disclosure relates to a method of serum-free culturing corneal limbal stromal stem cells, and a method of inducing corneal limbal stromal stem cells to form spheres and differentiate in vitro.

BACKGROUND ART

Cornea is a layer of transparent tissue in the front of an eyeball and spatially has a certain radius of curvature. Physiologically speaking, a cornea includes a transparent corneal area in the middle and a corneal limbal area in the periphery. The transparent corneal area in the middle includes five layers in total, which are respectively corneal epithelium, Bowman's membrane, stroma, Descemet's membrane and endothelium from outside to inside. Among them, the stroma accounts for 90% of the cornea thickness and is mainly composed of type I collagen, type V collagen, adhesives and corneal stromal cells. In auxology, corneal stromal cell origins from neural crest cell. After birth, these cells do not proliferate or divide, instead, they usually stay stationary. Such corneal stromal cells can keep the cornea intact and transparent by secreting ECM. Damage to the cornea or damage to the corneal stroma caused by bacterial or fungal keratitis, alkali burn or other diseases may lead to leukoma. When it occurs, non-transparent areas in the cornea are created, which have a severe influence on the vision of patients. But there is not any effective therapy yet. Traditionally, leukoma is mainly treated by keratoplasty. However, there are a series of problems with keratoplasty, for example, insufficient donor sources, rejection and various complications after operation, which make the clinical efficacy of such treatment is not satisfactory. Therefore, treating leukoma by transplanting with corneal limbal stromal stem cells cultured in vitro has become a concern in recent years.

Currently, corneal limbal stromal stem cells are mainly cultured via in vitro expansion of primary cells obtained from a corneal limbal tissue by enzyme digestion. It is extremely important to keep the stemness and characters of stromal stem cells after culturing in vitro. It is still a subject remaining urgent to be solved in cell engineering.

SUMMARY

An embodiment of present disclosure discloses a medium for corneal limbal stromal stem cells which contains a basic medium and additional components. The additional components include 50~150 IU of penicillin, 90~110 µg/mL of streptomycin, 40~60 µg/mL of gentamicin, ITS, 5~30 ng/mL of human recombinant EGF, 0.05~0.2 mM of L-ascorbic acid-2-phosphate, $1\times10^{-6}$~$1\times10^{-10}$ M of dexamethasone and 50~200 ng/mL of cholera toxin.

An embodiment of the present disclosure also discloses a medium for corneal limbal stromal stem cells to form spheres, which contains a basic medium and additional components. The additional components include 50~150 IU of penicillin, 90~110 µg/mL of streptomycin, 40~60 µg/mL of gentamicin, 5~30 ng/mL of human recombinant EGF, 0.5~4 mM of L-glutamine, 0.5%~5% of B27 and ITS.

An embodiment of the present disclosure also discloses a medium for corneal limbal stromal cells, which contains a basic medium and additional components. The additional components include 50~150 IU of penicillin, 90~110 µg/mL of streptomycin, 40~60 µg/mL of gentamicin, ITS, 0.2~2 mM of L-ascorbic acid-2-phosphate and 10~200 ng/mL of human recombinant FGF2.

An embodiment of the present disclosure also discloses a medium combination for serum-free culturing corneal limbal stromal stem cells and for inducing them to form spheres and differentiate in vitro, which is the combination of the above medium for corneal limbal stromal stem cells and the above medium for corneal limbal stromal stem cells to form spheres or the combination of the above medium for corneal limbal stromal stem cells and the medium for corneal limbal stromal cells.

An embodiment of the present disclosure also discloses a method of serum-free culturing corneal limbal stromal stem cells in vitro, which includes cleaning and cutting a corneal limbal tissue, performing enzymolysis, and placing the products from the enzymolysis into the medium for corneal limbal stromal stem cells for culture.

An embodiment of the present disclosure also discloses an in vitro culture method for corneal limbal stromal stem cells to form spheres, which includes culturing the corneal limbal stromal stem cells to P1~P5 generation, cleaning and digesting them, and then placing the products from the digestion into the medium for corneal limbal stromal stem cells to form spheres for culture.

An embodiment of the present disclosure also discloses a method of culturing corneal limbal stromal cells in vitro, which includes culturing corneal limbal stromal stem cells to P1~P5 generation, cleaning and digesting them, placing the products from the digestion into the medium for corneal limbal stromal stem cells for culture, and then transferring them into the medium for corneal limbal stromal cells after 12~36 h of culture.

An embodiment of the present disclosure also discloses a method of serum-free culturing corneal limbal stromal stem cells and inducing them to form spheres in vitro, which includes serum-free in vitro culture of corneal limbal stromal stem cells and in vitro culture for corneal limbal stromal cells to form spheres, specifically, culturing corneal limbal stromal stem cells to P1~P5 generation using the above method, cleaning and digesting them, and then placing the products from the digestion into the medium for corneal limbal stromal stem cells to form spheres for culture.

An embodiment of the present disclosure also discloses a method of serum-free culturing corneal limbal stromal stem cells and inducing them to differentiate in vitro, which includes serum-free in vitro culture of corneal limbal stromal stem cells and in vitro culture of corneal limbal stromal cells, specifically, culturing corneal limbal stromal stem cells to P1~P5 generation using the above method, cleaning and digesting them, placing the products from the digestion into the medium of corneal limbal stromal stem cells for culture, and then transferring them into the medium of corneal limbal stromal cells after 12~36 h of culture.

DETAILED DESCRIPTION OF EMBODIMENTS

Figure 1:
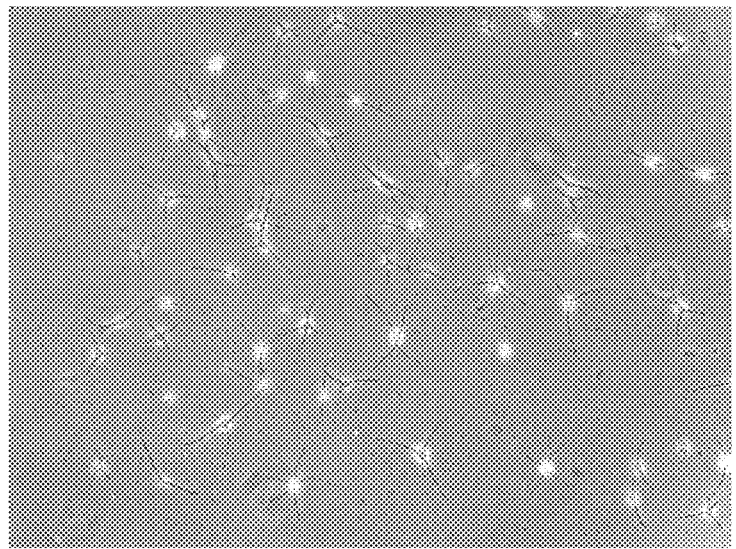
FIG. 1 is a diagram of cell morphology of serum-free cultured corneal limbal stromal stem cells.

The goal of the present disclosure is to overcome the above defects in the prior art by providing a method of serum-free culturing corneal limbal stromal stem cells, which keeps the stemness and specificity of corneal limbal stromal stem cells after in vitro expansion. It ensures that corneal stromal stem cells cultured in vitro can differentiate into corneal stromal cells for repairing injuries after being transplanted back to the body, so as to treat keratopathy e.g. leukoma and create suitable conditions for further clinical transplantation.

An embodiment of the present disclosure provides a medium for corneal limbal stromal stem cells.

An embodiment of the present disclosure provides a medium for corneal limbal stromal stem cells to form spheres.

An embodiment of the present disclosure provides a medium for corneal limbal stromal cells.

An embodiment of the present disclosure provides a medium for inducing corneal limbal stromal stem cells to form spheres or differentiate into corneal limbal stromal cells in vitro.

An embodiment of the present disclosure provides a method of serum-free culturing corneal limbal stromal stem cells in vitro using the above medium for corneal limbal stromal stem cells.

An embodiment of the present disclosure provides a culture method of inducing corneal limbal stromal stem cells to form spheres in vitro, i.e. an in vitro culture method to obtain corneal limbal stromal stem cell spheres using the above medium for corneal limbal stromal stem cells and the above medium for corneal limbal stromal cells to form spheres.

An embodiment of the present disclosure provides a culture method of inducing corneal limbal stromal stem cells to differentiate into corneal limbal stromal cells in vitro, i.e. an in vitro culture method to obtain corneal limbal stromal cells using the above medium for corneal limbal stromal stem cells and the above medium for corneal limbal stromal cells.

The above embodiments of the present disclosure are achieved by the following technical solutions.

The present disclosure relates to a medium for corneal limbal stromal stem cells which contains a basic medium and additional components. The additional components include 50~150 IU of penicillin, 90~110 μg/mL of streptomycin, 40~60 μg/mL of gentamicin, ITS, 5~30 ng/mL of human recombinant EGF, 0.05~0.2 mM of L-ascorbic acid-2-phosphate, $1 \times 10^{-6}$~$1 \times 10^{-10}$ M of dexamethasone and 50~200 ng/mL of cholera toxin.

In the present disclosure, the basic medium refers to a serum-free medium which can provide essential nutrient substances for corneal limbal stromal stem cells or corneal limbal stromal cells, and covers all well-known media suitable for culturing corneal limbal stromal stem cells or corneal limbal stromal cells in the field of corneal limbal stromal cell culture.

Preferably, the basic medium in the present disclosure is low-glucose DMEM, MCDB-201 and/or Advanced DMEM.

More preferably, the basic medium mentioned in the medium for corneal limbal stromal stem cells is low-glucose DMEM and/or MCDB-201.

Preferably, the additional components are present in the medium at the following concentrations respectively: 100 IU of penicillin, 100 μg/mL of streptomycin, 50 μg/mL of gentamicin, ITS, 20 ng/mL of human recombinant EGF, 0.1 mM of L-ascorbic acid-2-phosphate, $1 \times 10^{-8}$ M of dexamethasone and 100 ng/mL of cholera toxin.

More preferably, the medium for corneal limbal stromal stem cells is formulated by the following proportions: every 500 mL medium contains 5 mL of 10× Penicillin-Streptomycin Solution, 500 μL of gentamicin, 5 mL of ITS, 1 mL of human recombinant EGF, 1 mL of L-ascorbic acid-2-phosphate, 1 mL of cholera toxin and 288 mL of low-glucose DMEM, the rest being MCDB-201.

The present disclosure also relates to a medium for corneal limbal stromal stem cells to form spheres, which contains a basic medium and additional components. The additional components include 50~150 IU of penicillin, 90~110 μg/mL of streptomycin, 40~60 μg/mL of gentamicin, 5~30 ng/mL of human recombinant EGF, 0.5~4 mM of L-glutamine, 0.5%~5% of B27 and ITS.

Preferably, the basic medium mentioned in the medium for corneal limbal stromal stem cells to form spheres is Advanced DMEM.

Preferably, the additional components are present in the medium at the following concentrations respectively: 100 IU of penicillin, 100 μg/mL of streptomycin, 50 μg/mL of gentamicin, 20 ng/mL of human recombinant EGF, 2 mM of L-glutamine, 2% of B27 and ITS.

More preferably, the medium for corneal limbal stromal stem cells to form spheres is formulated by the following proportions: every 500 mL medium contains 5 mL of 10×

Penicillin-Streptomycin Solution, 500 µL of gentamicin, 5 mL of ITS, 1 mL of human recombinant EGF, 5 mL of L-glutamine and 5 mL of B27, the rest being Advanced DMEM.

The present disclosure also relates to a medium for corneal limbal stromal cells, which contains a basic medium and additional components. The additional components include 50~150 IU of penicillin, 90~110 µg/mL of streptomycin, 40~60 µg/mL of gentamicin, ITS, 0.2~2 mM of L-ascorbic acid-2-phosphate and 10~200 ng/mL of human recombinant FGF2.

Preferably, the basic medium mentioned in the medium for corneal limbal stromal cells is low-glucose DMEM.

Preferably, the additional components are present in the medium at the following concentrations: 100 IU of penicillin, 100 µg/mL of streptomycin, 50 µg/mL of gentamicin, ITS, 1 mM of L-ascorbic acid-2-phosphate and 100 ng/mL of human recombinant FGF2.

More preferably, the medium for corneal limbal stromal cells is formulated by the following proportions: every 500 mL medium contains 5 mL of 10× Penicillin-Streptomycin Solution, 500 µL of gentamicin, 5 mL of ITS, 1 mL of L-ascorbic acid-2-phosphate and 1 mL of human recombinant FGF2, the rest being low-glucose DMEM.

In the present disclosure, ITS refers to Insulin, Transferrin, Selenium Solution. The ITS agent in the present disclosure is commercially available in Gbico, which is 100× solution and can be used after being diluted proportionally.

In the present disclosure, B27 refers to B27 additive. B27 additive is a serum free additive. The B27 additive in the present disclosure is commercially available in Gbico under the Item No. 12587010.

The present disclosure also relates to a medium combination for serum-free culturing corneal limbal stromal stem cells and for inducing them to form spheres and differentiate in vitro, which is the combination of the above medium for corneal limbal stromal stem cells and the above medium for corneal limbal stromal stem cells to form spheres or the combination of the above medium for corneal limbal stromal stem cells and the medium for corneal limbal stromal cells.

Specifically, the medium for inducing corneal limbal stromal stem cells to form spheres in vitro includes the medium for corneal limbal stromal stem cells and the medium for corneal limbal stromal stem cells to form spheres.

Specifically, the medium for inducing corneal limbal stromal stem cells to differentiate into corneal limbal stromal cells in vitro includes the medium for corneal limbal stromal stem cells and the medium for corneal limbal stromal cells.

The medium provided by the embodiments of the present disclosure is a serum-free medium with determined chemical components. It has a stable quality, is highly controllable in batches, and is promotable and marketable. It is the ideal medium for fundamental research and clinical application research of corneal limbal stromal stem cells and corneal limbal stromal cells.

The present disclosure also relates to a method of serum-free culturing corneal limbal stromal stem cells in vitro, which includes cleaning and cutting a corneal limbal tissue, performing enzymolysis, and placing the products from the enzymolysis into the medium for corneal limbal stromal stem cells for culture.

Preferably, the enzymolysis is done with type L collagenase.

Preferably, the type L collagenase is used at a concentration of 0.1~1 mg/mL for an enzymolysis time of 3~12 h.

Preferably, Matrigel is added before placing the products from the enzymolysis into the medium for the corneal limbal stromal stem cells for culture.

More preferably, after Matrigel is added, it is incubated under 37° C. for 10 min, and then isolated corneal limbal stromal stem cells are added.

The present disclosure also relates to an in vitro culture method for corneal limbal stromal stem cells to form spheres, which includes culturing the corneal limbal stromal stem cells to P1~P5 generation, cleaning and digesting them, and then placing the products from the digestion into the medium for corneal limbal stromal stem cells to form spheres for culture.

Preferably, the cleaning is done with PBS and the digestion is done with 0.01%~0.25% EDTA containing pancreatic enzyme.

Preferably, the culture plate is coated with Poly-HEMA two days before the products from the digestion are placed into the medium for corneal limbal stromal stem cells to form spheres.

More preferably, after the culture plate is coated with Poly-HEMA, it is incubated under 37° C. for 2~14 days, and then isolated corneal limbal stromal stem cells are added.

The present disclosure also relates to a method of culturing corneal limbal stromal cells in vitro, which includes culturing corneal limbal stromal stem cells to P1~P5 generation, cleaning and digesting them, placing the products from the digestion into the medium for corneal limbal stromal stem cells for culture, and then transferring them into the medium for corneal limbal stromal cells after 12~36 h of culture.

The present disclosure also relates to a method of serum-free culturing corneal limbal stromal stem cells and inducing them to form spheres in vitro, which includes serum-free in vitro culture of corneal limbal stromal stem cells and in vitro culture for corneal limbal stromal cells to form spheres, specifically, culturing corneal limbal stromal stem cells to P1~P5 generation using the above method, cleaning and digesting them, and then placing the products from the digestion into the medium for corneal limbal stromal stem cells to form spheres for culture.

The present disclosure also relates to a method of serum-free culturing corneal limbal stromal stem cells and inducing them to differentiate in vitro, which includes serum-free in vitro culture of corneal limbal stromal stem cells and in vitro culture of corneal limbal stromal cells, specifically, culturing corneal limbal stromal stem cells to P1~P5 generation using the above method, cleaning and digesting them, placing the products from the digestion into the medium of corneal limbal stromal stem cells for culture, and then transferring them into the medium of corneal limbal stromal cells after 12~36 h of culture.

As a preferred technical solution, the method of serum-free culturing corneal limbal stromal stem cells in vitro includes the following steps.

S11, which is to clean a corneal limbal tissue using DMEM, cut it for enzymolysis, perform enzymolysis under 37° C. for 3~12 h using type L collagenase as an enzyme with a concentration of 0.1~1 mg/mL, filter with a 40 µm cell strainer to remove the residual tissue blocks, add 10 mg/mL of isometric Trypsin inhibitor to terminate the enzymolysis, centrifuge at 1500 rpm for 5 min, and discard the supernatant;

S12, which is to resuspend the corneal limbal stromal stem cells obtained from the enzymolysis and centrifugation using the above medium for corneal limbal stromal stem cells;

S13, which is to plate 10% Matrigel solution in a 24-well plate, leave it to stand under 37° C. for 10 min, and aspirate the remaining Matrigel solution; and S14, which is to grow the resuspended corneal limbal stromal stem cells on the 24-well plate with 10% Matrigel, culture them under 37° C. and 5% $CO_2$ for 12~24 h for adherence, and replace the solution the next day.

As a preferred technical solution, the method of serum-free culturing corneal limbal stromal stem cells and inducing them to form spheres in vitro includes the following steps.

S21, which is to aspirate and discard the liquid when the P1~P3 generation of cells from the corneal limbal stromal stem cells cultured in S14 described above grow to a confluence of 80%~90%, wash them with PBS, digest them with 0.01%~0.25% EDTA containing pancreatic enzyme, add 10 mg/mL of isometric Trypsin inhibitor to terminate the enzymolysis, centrifuge at 1500 rpm for 5 min, and then discard the supernatant;

S22, which is to resuspend the corneal limbal stromal stem cells obtained from the enzymolysis and centrifugation using the above medium for corneal limbal stromal stem cells to form spheres;

S23, which is to place 120 mg/mL Poly-HEMA solution under 37° C. on a shaker overnight for complete dissolution, plate the solution in a 12-well plate and leave the plate under 37° C. to stand for 48 h before use;

S24, which is to grow the resuspended corneal limbal stromal stem cells on a 12-well plate with 120 mg/mL Poly-HEMA solution, culture under 37° C. and 5% $CO_2$ and observe the cell status the next day; and S25, which is to replace the solution with the medium for corneal limbal stromal stem cells to form sphere and culture for about 7 days.

As a preferred technical solution, the method of serum-free culturing corneal limbal stromal stem cells and inducing them to differentiate in vitro includes the following steps.

S31, which is to aspirate and discard the liquid when the P2~P4 generation of cells from the corneal limbal stromal stem cells cultured in S14 described above grow to a confluence of 80%~90%, wash them with PBS, digest them with 0.01%~0.25% EDTA containing pancreatic enzyme, add 10 mg/mL of isometric Trypsin inhibitor to terminate the enzymolysis, centrifuge at 1500 rpm for 5 min, and then discard the supernatant;

S32, which is to resuspend the corneal limbal stromal stem cells obtained from the enzymolysis and centrifugation using the above medium for corneal limbal stromal stem cells;

S33, which is to plate 10% Matrigel solution in a 24-well plate, leave it to stand in an incubator under 37° C. for 10 min, and aspirate the remaining Matrigel solution;

S34, which is to grow the resuspended corneal limbal stromal stem cells in the 24-well plate with 10% Matrigel and place the plate in an incubator under 37° C. and 5% $CO_2$ for culture;

S35, which is to replace with the above medium of corneal limbal stromal cell the next day to induce differentiation and observe the cell growth status under a microscope; and S36, which is to replace the solution with the medium of corneal limbal stromal cell every 2 days and culture them to differentiate for about 7 days.

Compared with the prior art, the present disclosure provides the following beneficial effects.

The serum-free medium used in the present disclosure can provide a stable in vitro expansion of corneal limbal stromal stem cells, create a culture system for stem cells to form spheres in vitro, and express corresponding stem cell Marker. It is proved by experiments that the corneal limbal stromal stem cells cultured in vitro in the present disclosure have stemness. In addition, it successfully creates a system of inducing them to differentiate into corneal limbal stromal cells and can specifically highly express the specific Marker of corneal limbal stromal cells. This fully testifies that a differentiation system established in the present disclosure is successful. Compared with other serum containing culture methods, the present disclosure avoids the influence of serum on the experimental research, clarifies the effect that each of the components in the medium has on corneal limbal stromal cell culture, improves the reproducibility of cell culture and experiment results, and is easier to purify the cell products, making it easy to industrialize. Therefore, it has a broad prospect of application and development.

Below the present disclosure will be further explained with reference to specific examples, but such examples do not limit the present disclosure in any way. Without departing from the spirit and essence of the present disclosure, simple modifications or replacements made to the methods, steps or conditions of the present disclosure fall within the scope of the present disclosure. The technical means used in the examples are all conventional ones well-known to those skilled in the art if not particularly specified.

The agents and materials used in the following examples are all commercially available unless otherwise specified.

ITS in the present disclosure is commercially available in Gbico, which is 100× solution and can be used after being diluted proportionally.

Example 1 A Medium for Corneal Limbal Stromal Stem Cells and Culture Method Thereof 1. Medium Formula A medium for corneal limbal stromal stem cells, consisting of the following components:

every 500 mL medium contains 5 mL of 10× Penicillin-Streptomycin Solution, 500 µL of gentamicin, 5 mL of ITS, 1 mL of human recombinant EGF, 1 mL of L-ascorbic acid-2-phosphate, 1 mL of cholera toxin and 288 mL of low-glucose DMEM, the rest being MCDB-201.

The components are present in the medium at the following concentrations respectively: 100 IU of penicillin, 100 µg/mL of streptomycin, 50 µg/mL of gentamicin, ITS, 20 ng/mL of human recombinant EGF, 0.1 mM of L-ascorbic acid-2-phosphate, $1\times10^{-8}$ M of dexamethasone and 100 ng/mL of cholera toxin.

2. A Method of Serum-Free Culturing Corneal Limbal Stromal Stem Cells In Vitro, Including the Following Steps:

S11, which is to clean a corneal limbal tissue using DMEM, cut it with a scalpel for enzymolysis, place it in an incubator under 37° C. for enzymolysis for 3~12 h using type L collagenase at a concentration of 0.1~1 mg/mL, filter with a 40~70 µm cell strainer to remove the residual tissue blocks, add 10 mg/mL of isometric Trypsin inhibitor to terminate the enzymolysis, centrifuge at 1500 rpm for 5 min, and discard the supernatant;

S12, which is to resuspend the corneal limbal stromal stem cells obtained from the enzymolysis and centrifugation using the above medium for corneal limbal stromal stem cells;

S13, which is to plate 10% Matrigel solution in a 24-well plate, leave it to stand in an incubator under 37° C. for 10 min, and aspirate the remaining Matrigel solution; and S14, which is to grow the resuspended corneal limbal stromal stem cells in the 24-well plate with 10% Matrigel, place the plate in an incubator under 37° C. and 5% $CO_2$ for culture, replace the solution the next day and observe the cell growth status under a microscope.

3. Analysis of the Experiment Result.

As shown in FIG. 1, the primary corneal stromal stem cells cultured in serum-free medium in vitro present a cell morphology resembling multi-antenna dendritic cell morphology of nerve cells, which is more like the morphology of the neural crest cells they origin from. This indicates that such medium is more conducive to maintaining to the stemness of corneal stromal stem cells in vitro.

Example 2 A Medium for Corneal Limbal Stromal Stem Cells to Form Spheres and Culture Method Thereof 1. Medium Formula A medium for corneal limbal stromal stem cells to form spheres, consisting of the following components:

every 500 mL medium contains 5 mL of 10× Penicillin-Streptomycin Solution, 500 µL of gentamicin, 5 mL of ITS, 1 mL of human recombinant EGF, 5 mL of L-glutamine and 5 mL of B27, the rest being Advanced DMEM.

The components are present in the medium at the following concentrations respectively: 100 IU of penicillin, 100 µg/mL of streptomycin, 50 µg/mL of gentamicin, 20 ng/mL of human recombinant EGF, 2 mM of L-glutamine, 2% of B27 and ITS.

2. A Culture Method of Inducing Corneal Limbal Stromal Stem Cells In Vitro to Form Spheres, Including the Following Steps:

S21, which is to aspirate and discard the liquid when the P1~P3 generation of cells from the corneal limbal stromal stem cells cultured in S14 of Example 1 grow to a confluence of 80%~90%, wash them with PBS, digest them with 0.01%~0.25% EDTA containing pancreatic enzyme, add 10 mg/mL of isometric Trypsin inhibitor to terminate the enzymolysis, centrifuge at 1500 rpm for 5 min, and then discard the supernatant;

S22, which is to resuspend the corneal limbal stromal stem cells obtained from the enzymolysis and centrifugation using the above medium for corneal limbal stromal stem cells to form spheres;

S23, which is to place 120 mg/mL Poly-HEMA solution under 37° C. on a shaker overnight for complete dissolution, plate it in a 12-well plate and place the 12-well plate in an incubator under 37° C. and leave to stand for 48 h before use;

S24, which is to grow the resuspended corneal limbal stromal stem cells on a 12-well plate with 120 mg/mL Poly-HEMA solution, place the 12-well plate in an incubator under 37° C. and 5% $CO_2$ for culture and observe the cell status the next day; and S25, which is to replace the solution with medium for corneal limbal stromal stem cells to form spheres, culture for 7 days for them to form spheres and then collect cell RNA.

3. Analysis of the Experiment Result.

Figure 2:
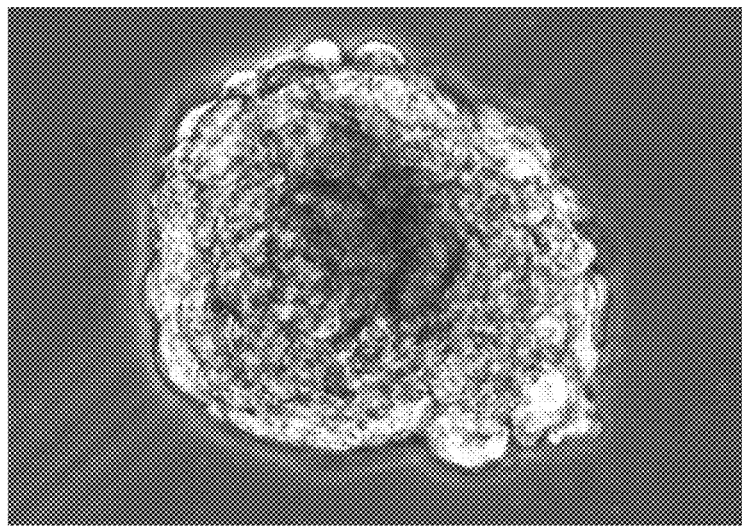
FIG. 2 is a diagram of cell morphology of sphere formation cultured corneal limbal stromal stem cells.

As shown in FIG. 2, when cultured to form spheres, corneal stromal stem cells cultured in vitro can grow as spheres and have good stemness.

Example 3 A Medium for Corneal Limbal Stromal Cells and Culture Method Thereof

1. Medium Formula

A medium for corneal limbal stromal cells, consisting of the following components:

Every 500 mL medium contains 5 mL of 10× Penicillin-Streptomycin Solution, 500 µL of gentamicin, 5 mL of ITS, 1 mL of L-ascorbic acid-2-phosphate and 1 mL of human recombinant FGF2, the rest being low-glucose DMEM.

The components are present in the medium at the following concentrations respectively: 100 IU of penicillin, 100 µg/mL of streptomycin, 50 µg/mL of gentamicin, ITS, 1 mM of L-ascorbic acid-2-phosphate and 100 ng/mL of human recombinant FGF2.

2. A Culture Method of Inducing Corneal Limbal Stromal Stem Cells In Vitro to Differentiate into Corneal Limbal Stromal Cells, Including the Following Steps:

S31, which is to aspirate the liquid when the P2~P4 generation of cells from the corneal limbal stromal stem cells cultured in S14 grow to a confluence of 80%~90%, wash them with PBS, digest them with 0.01%~0.25% EDTA containing pancreatic enzyme, add 10 mg/mL of isometric Trypsin inhibitor to terminate the enzymolysis, centrifuge at 1500 rpm for 5 min, and then discard the supernatant;

S32, which is to resuspend the corneal limbal stromal stem cells obtained from the enzymolysis and centrifugation using the above medium for corneal limbal stromal stem cells;

S33, which is to plate 10% Matrigel solution in a 24-well plate, leave it to stand in an incubator under 37° C. for 10 min, and aspirate the remaining Matrigel solution;

S34, which is to grow the resuspended corneal limbal stromal stem cells in the 24-well plate with 10% Matrigel and place the 24-well plate in an incubator under 37° C. and 5% $CO_2$ for culture;

S35, which is to replace with the above medium for corneal limbal stromal cell the next day to induce differentiation and observe the cell growth status under a microscope; and S36, which is to replace the solution with the medium for corneal limbal stromal cell every 2 days, culture them to differentiate for about 7 days and collect cell RNA.

3. Analysis of the Experiment Result.

(1) Observation of Cell Morphology

Figure 3:
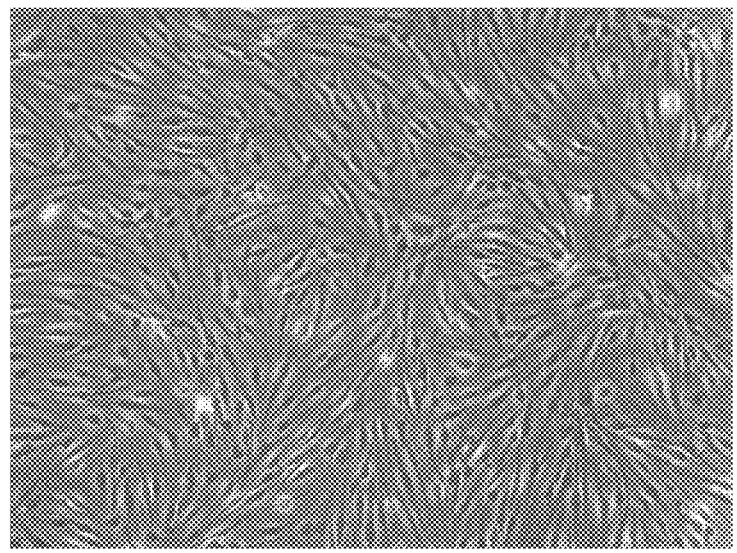
FIG. 3 is a diagram of cell morphology of corneal limbal stromal cells.

As shown in FIG. 3, when induced to differentiate, corneal stromal stem cells cultured in vitro present the morphology of corneal limbal stromal cells in stationary phase, and express specific Marker of corneal limbal stromal cells. This indicates that the differentiation culture provides good stemness and specificity.

Comparative Example 1 Positive Control (Fetal Calf Serum Containing Medium)

The experimental method is the same as that in Example 1, except that the medium for corneal limbal stromal stem cells used in this example contains fetal calf serum and specifically consists of 216 mL of Ham's F12, 216 mL of DMEM, 5 mL of 100× Penicillin-Streptomycin Solution and 63 mL of fetal calf serum.

Figure 4:
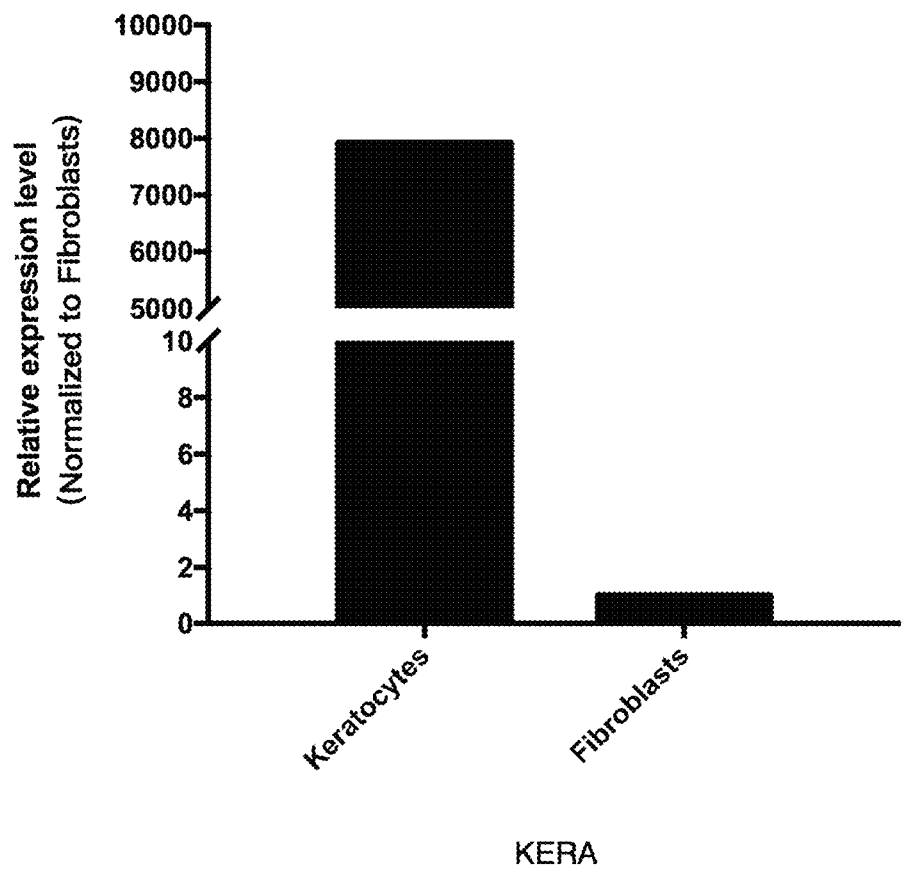
FIG. 4 is a diagram showing the QPCR result of specific marker KERA of corneal limbal stromal cells (the corneal limbal stromal cells cultured in a serum-free medium as described in the present disclosure are marked as keratocytes, and the corneal limbal stromal cells cultured in serum containing medium are marked as Fibroblasts).
Figure 5:
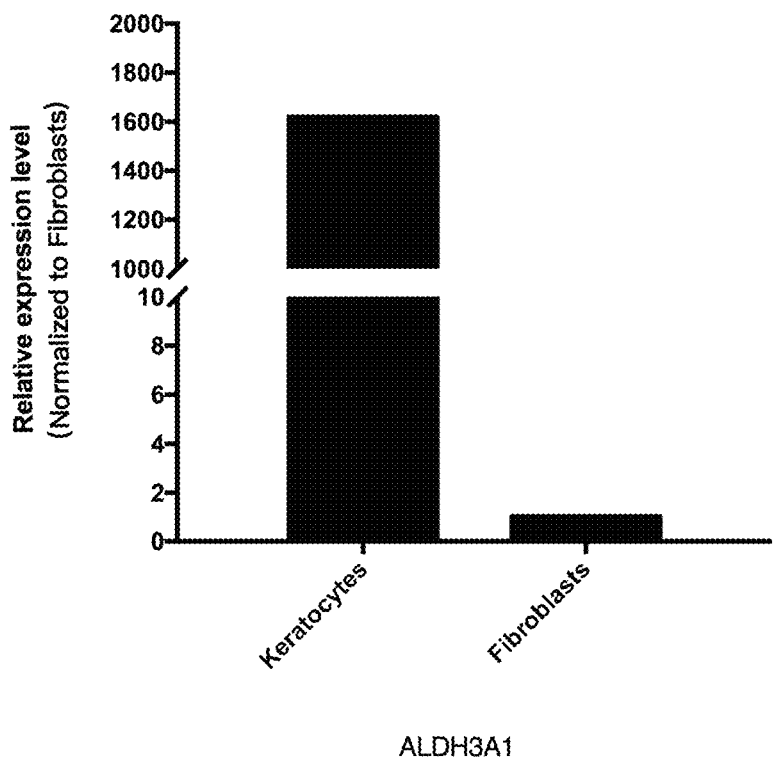
FIG. 5 is a diagram showing the QPCR result of specific marker ALDH3A1 of corneal limbal stromal cells (the corneal limbal stromal cells cultured in a serum-free medium as described in the present disclosure are marked as keratocytes, and the corneal limbal stromal cells cultured in serum containing medium are marked as Fibroblasts).
Figure 6:
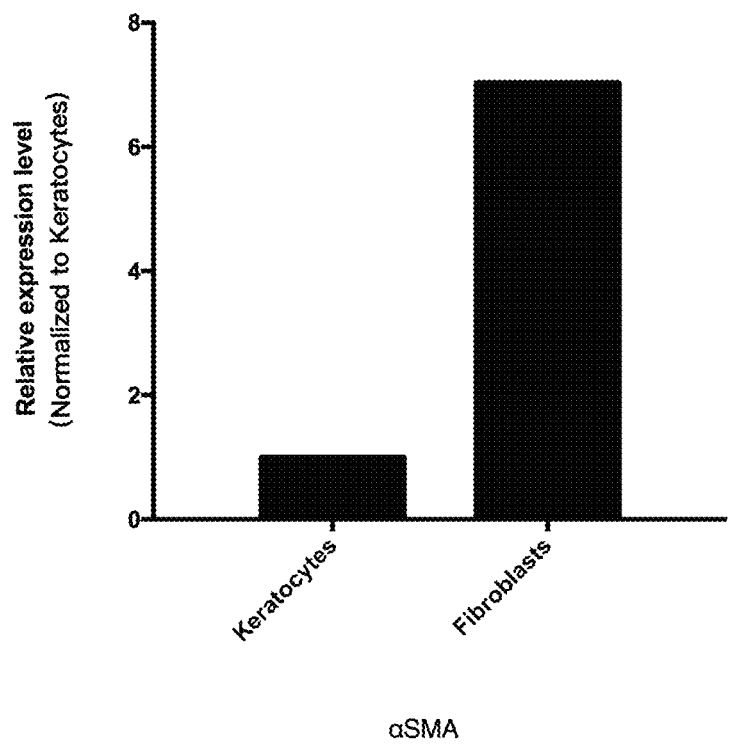
FIG. 6 is a diagram showing the QPCR result of specific marker αSMA of fibroblasts (the corneal limbal stromal cells cultured in a serum-free medium as described in the present disclosure are marked as keratocytes, and the corneal limbal stromal cells cultured in serum containing medium are marked as Fibroblasts).
Figure 7:
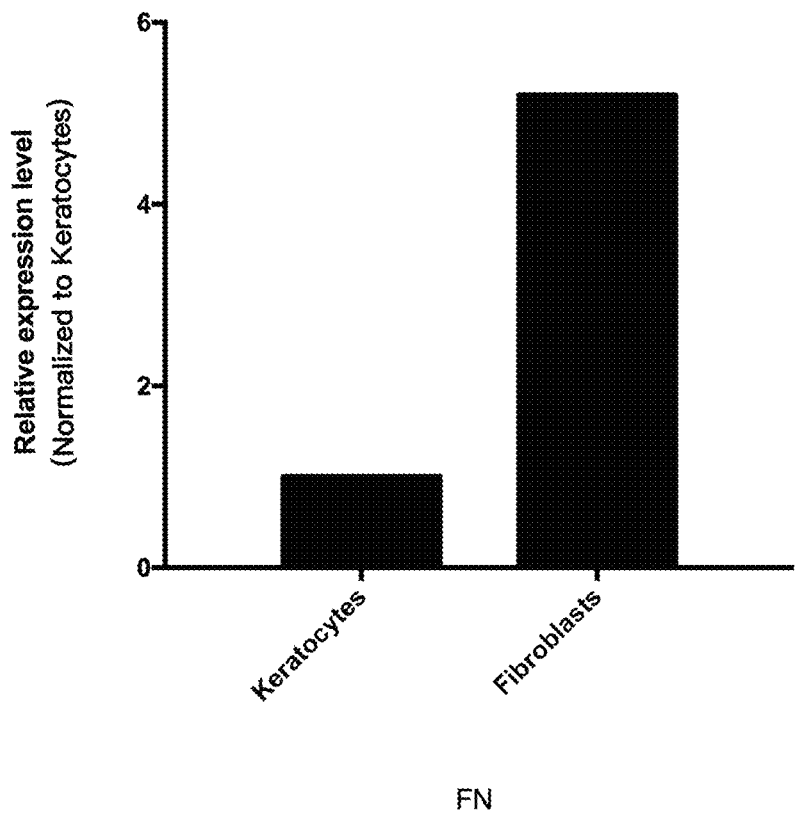
FIG. 7 is a diagram showing the QPCR result of specific marker FN of fibroblasts (the corneal limbal stromal cells cultured in a serum-free medium as described in the present disclosure are marked as keratocytes, and the corneal limbal stromal cells cultured in serum containing medium are marked as Fibroblasts).
Figure 8:
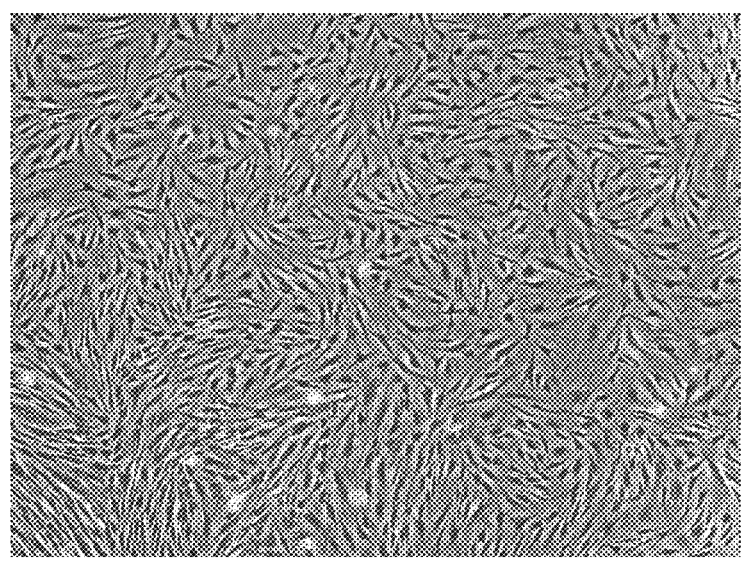
FIG. 8 is a diagram of cell morphology of corneal limbal stromal cells cultured in serum containing medium.

It is found that compared with serum containing culture method, the corneal limbal stromal stem cells cultured by using the serum-free medium and culture method thereof according to the present disclosure not only have a morphology more similar to the neural crest cells they biologically origin from (FIG. 1), but also can specifically express Marker of stem cells. In addition, as shown in FIG. 4 and FIG. 5, when induced to differentiate into corneal limbal stromal cells, they can specifically express Marker of corneal limbal stromal cells (KERA and ALDH3A1). However, as shown in FIGS. 6, 7 and 8, the cells cultured with serum containing medium are more like fibrocytes cultured in vitro. They not only present as a spindle morphology of fibrocytes, but also highly express Marker of fibroblasts (e.g. FN and αSMA). The results show that cells cultured with the medium for culturing corneal limbal stromal stem cells in vitro in a serum-free manner and culture method thereof according to the present disclosure have a higher stemness and specificity and a better cell differentiation performance.

Comparative Example 2

1. Influence on Growth of Corneal Limbal Stromal Stem Cells (1) Influence of Different Component Concentrations on Growth of Corneal Limbal Stromal Stem Cells Detection of influence of varied concentrations of medium components on the growth of corneal limbal stromal stem cells: corneal limbal stromal stem cells were cultured according to the method of Example 1 using the medium as shown in Table 1 respectively; three parallel controls were prepared for each group; they were counted 24 hours later. Table 1 shows the result.

TABLE 1

Influence of different component concentrations on growth of corneal limbal stromal stem cells

|  | Group 1 | Group 2 | Group 3 | Group 4 | Group 5 |
| --- | --- | --- | --- | --- | --- |
| Penicillin (IU) | 20 | 50 | 100 | 150 | 170 |
| Streptomycin (μg/mL) | 40 | 90 | 100 | 110 | 130 |
| Gentamicin (μg/mL) | 10 | 40 | 50 | 60 | 80 |
| Human recombinant EGF (ng/mL) | 1 | 5 | 20 | 30 | 50 |
| L-ascorbic acid-2-phosphate (mM) | 0.01 | 0.05 | 0.1 | 0.2 | 0.5 |
| Dexamethasone (M) | $1 \times 10^{-12}$ | $1 \times 10^{-10}$ | $1 \times 10^{-8}$ | $1 \times 10^{-6}$ | $1 \times 10^{-4}$ |
| Cholera toxin (ng/mL) | 20 | 50 | 100 | 200 | 300 |
| Cell counting (/mL) | $1 \times 10^3$ | $5 \times 10^3$ | $6 \times 10^4$ | $8 \times 10^3$ | $3 \times 10^3$ |

The study shows that the corneal limbal stromal stem cells grow better with 50~150 IU of penicillin, 90~110 μg/mL of streptomycin, 40~60 μg/mL of gentamicin, 5~30 ng/mL of human recombinant EGF, 0.05~0.2 mM of L-ascorbic acid-2-phosphate, $1 \times 10^{-6}$~$1 \times 10^{-10}$ M of dexamethasone and 50~200 ng/mL of cholera toxin and the corneal limbal stromal stem cells grow best with 100 IU of penicillin, 100 μg/mL of streptomycin, 50 μg/mL of gentamicin, 20 ng/mL of human recombinant EGF, 0.1 mM of L-ascorbic acid-2-phosphate, $1 \times 10^{-8}$ M of dexamethasone and 100 ng/mL of cholera toxin.

(2) Influence of Different Components on Growth of Corneal Limbal Stromal Stem Cells Detection of influence of changes of medium components on the growth of corneal limbal stromal stem cells: the other conditions are the same as those in Example 1, corneal limbal stromal stem cells were cultured using the medium as shown in Table 2 respectively; three parallel controls were prepared for each group; they were counted 24 hours later. Table 2 shows the result.

TABLE 2

Influence of different components on growth of corneal limbal stromal stem cells

| Group # | Component change | Cell counting (/mL) |
| --- | --- | --- |
| Group 6 | Penicillin removed | $1 \times 10^4$ |
| Group 7 | Streptomycin removed | $1 \times 10^4$ |

TABLE 2-continued

Influence of different components on growth of corneal limbal stromal stem cells

| Group # | Component change | Cell counting (/mL) |
| --- | --- | --- |
| Group 8 | Gentamicin removed | $1 \times 10^4$ |
| Group 9 | Human recombinant EGF removed | $1 \times 10^3$ |
| Group 10 | L-ascorbic acid-2-phosphate removed | $1 \times 10^3$ |
| Group 11 | Dexamethasone removed | $1 \times 10^3$ |
| Group 12 | Cholera toxin removed | $1 \times 10^3$ |
| Group 13 | ITS removed | $1 \times 10^3$ |
| Group 14 | Dexamethasone replaced with hydrocortisone | $2 \times 10^3$ |
| Group 15 | L-ascorbic acid-2-phosphate replaced with insulin | $1 \times 10^3$ |

As can be seen from Table 2, penicillin, streptomycin, gentamicin, human recombinant EGF, L-ascorbic acid-2-phosphate, dexamethasone, cholera toxin and ITS in the serum-free medium for corneal limbal stromal stem cells all play an important role in the growth of corneal limbal stromal stem cells. These components interact with each other and none of them is dispensable.

2. Influence on Sphere Formation of Corneal Limbal Stromal Stem Cells (1) Influence of Varied Concentrations of Components on Sphere Formation of Corneal Limbal Stromal Stem Cells Detection of influence of varied concentrations of each of medium components on the sphere formation of corneal limbal stromal stem cells: corneal limbal stromal stem cells were cultured according to the method of Example 2 using the medium as shown in Table 3 respectively; three parallel controls were prepared for each group; they were counted 24 hours later. Table 3 shows the result.

TABLE 3

Influence of different component concentrations on sphere formation of corneal limbal stromal stem cells

|  | Group 21 | Group 22 | Group 23 | Group 24 | Group 25 |
| --- | --- | --- | --- | --- | --- |
| Penicillin (IU) | 20 | 50 | 100 | 150 | 170 |
| Streptomycin (μg/mL) | 40 | 90 | 100 | 110 | 130 |
| Gentamicin (μg/mL) | 10 | 40 | 50 | 60 | 80 |
| Human recombinant EGF (ng/mL) | 1 | 5 | 20 | 30 | 50 |
| L-glutamine (mM) | 0.01 | 0.5 | 2 | 4 | 6 |
| B27 and ITS (%) | 0.1% | 0.5% | 2 | 5% | 10% |
| Cell counting (/mL) | $1 \times 10^2$ | $2 \times 10^2$ | $1 \times 10^3$ | $4 \times 10^2$ | $1 \times 10^2$ |

The study shows that the corneal limbal stromal stem cells form spheres better with 50~150 IU of penicillin, 90~110

μg/mL of streptomycin, 40~60 μg/mL of gentamicin, 5~30 ng/mL of human recombinant EGF, 0.5~4 mM of L-glutamine, and 0.5%~5% of B27 and ITS, and the corneal limbal stromal stem cells form spheres best with 100 IU of penicillin, 100 μg/mL of streptomycin, 50 μg/mL of gentamicin, 20 ng/mL of human recombinant EGF, 2 mM of L-glutamine, and 2% of B27 and ITS.

(2) Influence of Different Components on Sphere Formation of Corneal Limbal Stromal Stem Cells Detection of influence of changes of medium components on the sphere formation of corneal limbal stromal stem cells: the other conditions are the same as those in Example 2, corneal limbal stromal stem cells were cultured using the medium as shown in Table 4 respectively; three parallel controls were prepared for each group; they were counted 24 hours later. Table 4 shows the result.

TABLE 4

Influence of different components on sphere formation of corneal limbal stromal stem cells

| Group # | Component variation | Cell counting (/mL) |
| --- | --- | --- |
| Group 26 | Penicillin removed | $8 \times 10^2$ |
| Group 27 | Streptomycin removed | $8 \times 10^2$ |
| Group 28 | Gentamicin removed | $8 \times 10^2$ |
| Group 29 | Human recombinant EGF removed | $1 \times 10^2$ |
| Group 30 | L-glutamine removed | $1 \times 10^2$ |
| Group 31 | B27 removed | $1 \times 10^2$ |
| Group 32 | ITS removed | $1 \times 10^2$ |
| Group 33 | Gentamicin replaced with amphotericin B2 | $7 \times 10^2$ |
| Group 34 | L-glutamine replaced with L-asparagine | $1 \times 10^2$ |

As can be seen from Table 4, penicillin, streptomycin, gentamicin, human recombinant EGF, L-glutamine, B27 and ITS in the serum-free medium for corneal limbal stromal stem cells to form spheres all play an important role in the sphere formation of corneal limbal stromal stem cells. These components interact with each other and none of them is dispensable.

3. Influence on Growth of Corneal Limbal Stromal Cells (1) Influence of Varied Concentrations of Components on Growth of Corneal Limbal Stromal Cells Detection of influence of varied concentrations of each of medium components on the growth of corneal limbal stromal cells: corneal limbal stromal cells were cultured according to the method of Example 3 using the medium as shown in Table 5 respectively; three parallel controls were prepared for each group; they were counted 24 hours later. Table 5 shows the result.

TABLE 5

Influence of different component concentrations on growth of corneal limbal stromal cells

|  | Group 41 | Group 42 | Group 43 | Group 44 | Group 45 |
| --- | --- | --- | --- | --- | --- |
| Penicillin (IU) | 20 | 50 | 100 | 150 | 170 |
| Streptomycin (μg/mL) | 40 | 90 | 100 | 110 | 130 |
| Gentamicin (μg/mL) | 10 | 40 | 50 | 60 | 80 |
| L-ascorbic acid-2-phosphate (mM) | 0.05 | 0.2 | 1 | 2 | 4 |
| Human recombinant FGF2 (ng/mL) | 5 | 10 | 100 | 200 | 300 |
| Cell counting (/mL) | $1 \times 10^3$ | $5 \times 10^3$ | $5 \times 10^4$ | $2 \times 10^3$ | $1 \times 10^3$ |

The study shows that the corneal limbal stromal cells grow better with 50~150 IU of penicillin, 90~110 μg/mL of streptomycin, 40~60 μg/mL of gentamicin, 0.2~2 mM of L-ascorbic acid-2-phosphate and 10~200 ng/mL of human recombinant FGF2 and the corneal limbal stromal cells grow best with 100 IU of penicillin, 100 μg/mL of streptomycin, 50 μg/mL of gentamicin, 1 mM of L-ascorbic acid-2-phosphate and 100 ng/mL of human recombinant FGF2.

(2) Influence of Different Components on Growth of Corneal Limbal Stromal Cells

Detection of influence of changes of medium components on the growth of corneal limbal stromal cells: the other conditions are the same as those in Example 3, corneal limbal stromal stem cells were cultured using the medium as shown in Table 6 respectively; three parallel controls were prepared for each group; they were counted 24 hours later. Table 6 shows the result.

TABLE 6

Influence of different components on growth of corneal limbal stromal cells

| Group # | Component variation | Cell counting (/mL) |
| --- | --- | --- |
| Group 46 | Penicillin removed | $4 \times 10^4$ |
| Group 47 | Streptomycin removed | $4 \times 10^4$ |
| Group 48 | Gentamicin removed | $4 \times 10^4$ |
| Group 49 | L-ascorbic acid-2-phosphate removed | $1 \times 10^3$ |
| Group 50 | Human recombinant FGF2 removed | $1 \times 10^3$ |
| Group 51 | ITS removed | $1 \times 10^3$ |
| Group 52 | Gentamicin replaced with amphotericin B2 | $1 \times 10^4$ |
| Group 53 | L-ascorbic acid-2-phosphate replaced with vitamin B12 | $1 \times 10^3$ |

As can be seen from Table 6, penicillin, streptomycin, gentamicin, L-ascorbic acid-2-phosphate, human recombinant FGF2 and ITS in the serum-free medium for corneal limbal stromal stem cells to form spheres all play an important role in the growth of corneal limbal stromal cells. These components interact with each other and none of them is dispensable.

What is claimed is:

1. A medium for corneal limbal stromal stem cells, wherein the medium contains a basic medium and additional components, wherein the additional components comprise 50~150 IU of penicillin, 90~110 μg/mL of streptomycin, 40~60 μg/mL of gentamicin, ITS, 5~30 ng/mL of human recombinant Epidermal Growth Factor (EGF), 0.05~0.2 mM of L-ascorbic acid-2-phosphate, $1 \times 10^{-6}$~$1 \times 10^{-10}$ M of dexamethasone and 50~200 ng/mL of cholera toxin, and the basic medium comprises low-glucose DMEM.

2. A medium for corneal limbal stromal stem cells to form spheres, wherein the medium contains a basic medium and additional components, wherein the additional components comprise 50~150 IU of penicillin, 90~110 µg/mL of streptomycin, 40~60 µg/mL of gentamicin, 5~30 ng/mL of human recombinant EGF, 0.5~4 mM of L-glutamine, 0.5%~5% of B27 and ITS.

3. A medium for corneal limbal stromal cells, wherein the medium contains a basic medium and additional components, wherein the additional components comprise 50~150 IU of penicillin, 90~110 µg/ml of streptomycin, 40~60 µg/mL of gentamicin, ITS, 0.2~2 mM of L-ascorbic acid-2-phosphate and 10~200 ng/mL of human recombinant Fibroblast Growth Factor 2 (FGF2).

4. The medium for corneal limbal stromal stem cells to form sphere according to claim 2, wherein the basic medium is low-glucose DMEM, MCDB-201 and/or Advanced DMEM.

5. The medium for corneal limbal stromal cells according to claim 3, wherein the basic medium is low-glucose DMEM, MCDB-201 and/or Advanced DMEM.

6. The medium for corneal limbal stomal stem cells according to claim 1, wherein the medium for corneal limbal stromal stem cells is used in combination with a medium for corneal limbal stromal stem cells to form spheres, or with a medium for corneal limbal stromal cells,
wherein the medium for corneal limbal stromal stem cells to form sphere contains a basic medium and additional components, wherein the additional components comprise 50~150 IU of penicillin, 90~110 µg/mL of streptomycin, 40~60 µg/mL of gentamicin, 5~30 ng/mL of human recombinant EGF, 0.5~4 mM of L-glutamine, 0.5%~5% of B27 and ITS; and
the medium for corneal limbal stromal cells contains a basic medium and additional components, wherein the additional components comprise 50~150 IU of penicillin, 90µ110 µg/mL, 40~60 µg/mL of gentamicin, ITS, 0.2~2 mM of L-ascorbic acid-2-phosphate and 10~200 ng/mL of human recombinant FGF2.

7. The medium for corneal limbal stromal stem cells according to claim 1, wherein when the corneal limbal stomal stem cells are to be cultured in a serum-free manner in vitro, a corneal limbal tissue is cleaned, cut, and subjected to enzymolysis to obtain an enzymolysis product which is then cultured in the medium for corneal limbal stromal stem cells to obtain the corneal limbal stomal stem cells.

8. The medium for corneal limbal stromal stem cells to form sphere according to claim 2, wherein when the corneal limbal stromal stem cells are to be cultured to form spheres in vitro, corneal limbal stromal stem cells are cultured to P1~P5 generation, and subjected to cleaning and digestion to obtain a digestion product which is then cultured in the medium for corneal limbal stromal stem cells to form spheres.

9. The medium for corneal limbal stromal stem cells according to claim 1, wherein when the corneal limbal stomal cells are to be cultured in vitro, corneal limbal stromal stem cells are cultured to P1~P5 generation, and subjected to cleaning and digestion to obtain a digestion product which is then cultured in the medium for corneal limbal stromal stem cells for culture, and then transferred to a medium for corneal limbal stromal cells after 12~36 h of culture,
wherein the medium for corneal limbal stromal cells contains a basic medium and additional components, wherein the additional components comprise 50~150 IU of penicillin, 90~110 µg/mL, 40~60 µg/mL of gentamicin, ITS, 0.2~2 mM of L-ascorbic acid-2-phosphate and 10~200 ng/mL of human recombinant FGF2.

10. The medium for corneal limbal stomal cells according to claim 3, wherein when the corneal limbal stomal cells are to be cultured in vitro, corneal limbal stromal stem cells are cultured to P1~P5 generation, and subjected to cleaning and digestion to obtain a digestion product which is then cultured in a medium for corneal limbal stromal stem cells for culture, and then transferred to the medium for corneal limbal stromal cells after 12~36 h of culture,
wherein the medium for corneal limbal stromal stem cells contains a basic medium and additional components, wherein the additional components comprise 50~150 IU of penicillin, 90~110 µg/mL of streptomycin, 40~60 µg/mL of gentamicin, ITS, 5~30 ng/mL of human recombinant Epidermal Growth Factor (EGF), 0.05~0.2 mM of L-ascorbic acid-2-phosphate, $1\times10^{-6}$~$1\times10^{-10}$ M of dexamethasone and 50~200 ng/mL of cholera toxin.

11. The medium for corneal limbal stomal stem cells according to claim 1, wherein when the corneal limbal stomal stem cells are to be cultured in a serum-free manner and induced to form sphere in vitro, a corneal limbal tissue is cleaned, cut, and subjected to enzymolysis to obtain enzymolysis product which is then cultured in the medium for corneal limbal stromal stem cells to P1~P5 generation, and subjected to cleaning and digestion to obtain digestion product which is then cultured in a medium for corneal limbal stromal stem cells to form spheres,
wherein the medium for corneal limbal stromal stem cells to form sphere contains a basic medium and additional components, wherein the additional components comprise 50~150 IU of penicillin, 90~110 µg/mL of streptomycin, 40~60 µg/mL of gentamicin, 5~30 ng/mL of human recombinant EGF, 0.5~4 mM of L-glutamine, 0.5%~5% of B27 and ITS.

12. The medium for corneal limbal stromal stem cells to form sphere according to claim 2, wherein when the corneal limbal stromal stem cells are to be cultured in a serum-free manner and induced to form sphere in vitro, a corneal limbal tissue is cleaned, cut, and subjected to enzymolysis to obtain enzymolysis product, wherein the enzymolysis product is then cultured in a medium for corneal limbal stromal stem cells to P1~P5 generation, and subjected to cleaning and digestion to obtain digestion product which is then cultured in the medium for corneal limbal stromal stem cells to form spheres,
wherein the medium for corneal limbal stromal stem cells contains a basic medium and additional components, wherein the additional components comprise 50~150 IU of penicillin, 90~110 µg/mL of streptomycin, 40~60 µg/mL of gentamicin, ITS, 5~30 ng/mL of human recombinant Epidermal Growth Factor (EGF), 0.05~0.2 mM of L-ascorbic acid-2-phosphate, $1\times10^{-6}$~$1\times10^{-10}$ M of dexamethasone and 50~200 ng/mL of cholera toxin.

13. The medium for corneal limbal stromal stem cells according to claim 1, wherein when the corneal limbal stomal stem cells are to be cultured in a serum-free manner and induced to differentiate in vitro, a corneal limbal tissue is cleaned and cut, subjected to enzymolysis to obtain enzymolysis product, wherein the enzymolysis product is cultured in the medium for corneal limbal stromal stem cells to P1~P5 generation and subjected to cleaning and digestion to obtain digestion product which is then cultured in the medium for corneal limbal stromal stem cells, and then transferred to a medium for corneal limbal stromal cells after 12~36 h of culture, wherein the medium for corneal limbal stromal cells contains a basic medium and additional components, wherein the additional components comprise 50~150 IU of penicillin, 90~110 μg/mL, 40~60 μg/mL of gentamicin, ITS, 0.2~2 mM of L-ascorbic acid-2-phosphate and 10~200 ng/mL of human recombinant FGF2.

14. The medium for corneal limbal stomal cells according to claim 3, wherein when the corneal limbal stomal stem cells are cultured in a serum-free manner and induced to differentiate in vitro, a corneal limbal tissue is cleaned and cut, subjected to enzymolysis to obtain enzymolysis product which is cultured in a medium for corneal limbal stromal stem cells to P1~P5 generation and subjected to cleaning and digestion to obtain digestion product, wherein the enzymolysis product is then cultured in the medium for corneal limbal stromal stem cells, and then transferred to the medium for corneal limbal stromal cells after 12~36 h of culture, wherein the medium for corneal limbal stromal stem cells contains a basic medium and additional components, wherein the additional components comprise 50~150 IU of penicillin, 90~110 μg/mL of streptomycin, 40~60 μg/mL of gentamicin, ITS, 5~30 ng/mL of human recombinant Epidermal Growth Factor (EGF), 0.05~0.2 mM of L-ascorbic acid-2-phosphate, $1\times10^{-6}$~$1\times10^{-10}$ M of dexamethasone and 50~200 ng/mL of cholera toxin.

* * * * *